United States Patent [19]

Poupelin

[11] 4,147,806
[45] Apr. 3, 1979

[54] ANTI-INFLAMMATORY AND ANALGESIC MEDICAMENTS

[75] Inventor: Jean-Pierre Poupelin, Olivet, France

[73] Assignee: Laboratoires Creat, Vernouillet, France

[21] Appl. No.: 634,342

[22] Filed: Nov. 24, 1975

[30] Foreign Application Priority Data

Nov. 29, 1974 [FR] France .................. 74 39163

[51] Int. Cl.² .............. A61K 31/045; A61K 31/085; A61K 31/09; A61K 31/135
[52] U.S. Cl. ..................... 424/343; 260/340.5 R; 260/386; 260/562 P; 260/607 AR; 260/609 F; 260/571; 424/258; 424/263; 424/311; 424/324; 424/330; 424/335; 424/337; 424/340; 424/341; 546/152; 546/343; 568/719; 568/633; 568/707; 560/139
[58] Field of Search .............. 424/340, 341, 343, 330, 424/324

[56] References Cited
PUBLICATIONS

Bennett et al.; C. A. vol. 73 (1970) p. 308.
Thompson et al.; C. A. vol. 41 (1947) pp. 3902–3912.

Primary Examiner—Allen J. Robinson
Attorney, Agent, or Firm—Browdy and Neimark

[57] ABSTRACT

The active constituents of these medicaments are compounds of the general formula:

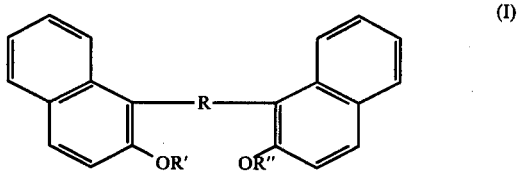

(I)

in which R represents a sulfur or oxygen atom or a >SO or >SO$_2$ radical or even a

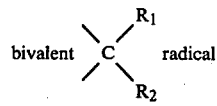

in which R$_1$ and R$_2$ which can be the same or different, represent a hydrogen atom or a hydroxyl, aryl, alkyl, arylalkyl, alkylaryl possibly halogenated or a heterocyclic radical, said radicals being substituted or unsubstituted, while R' and R'', which may be the same or different, represent a hydrogen atom, a metal such as an alkali or alkaline-earth metal or magnesium, or the ammonium ion or an alkyl radical, an aliphatic or aromatic acyl radical or a heterocyclic radical, which radicals may be substituted or unsubstituted. The process enables the products to be prepared in sufficiently pure form for therapeutic use. β-naphthol is reacted with a suitable aldehyde in an acetic medium, in the presence of hydrochloric acid added dropwise at between 5° and 10° C. Purification is by recrystallization from benzene or a mixture of solvents containing benzene.

13 Claims, No Drawings

ANTI-INFLAMMATORY AND ANALGESIC MEDICAMENTS

BACKGROUND OF THE INVENTION

1. Field of the Invention

The present invention relates to novel non-steroidal medicaments with anti-inflammatory and analgesic action, and to the process for their preparation.

The inflammatory process is perhaps among those which has been most investigated, since the illnesses involving it, such as rheumatism, gout, etc., constitute the principal causes of absence from work. Also, from the therapeutic aspect, a very large number of medicaments have been proposed, among which the most important group is constituted by the anti-inflammatory agents.

2. Description of the Prior Art

A great many substances have thus been synthesized and proposed, among which number may be mentioned the family of pyrazolone and its derivatives, [notably phenylbutazone or 4-butyl-1, 2-diphenyl-3, 5-pyrazolidinedione (U.S. Pat. No. 2,562,830); oxyphenbutazone or p-hydroxyphenylbutazone (U.S. Pat. No. 2,745,783); mofebutazone or 4-butyl-1-phenyl-3, 5-pyrazolidinedione (British Pat. No. 839,057); sulfinpyrazone or sulfoxyphenylpyrazolidine (Helvetica Chimica Acta 44 p. 232, 1961) etc.]; the family of indole and its derivatives [such as indomethacine, (U.S. Pat. No. 3,161,654) etc.]; the family of derivatives of anthranilic acids (mefenamic, flufenamic, clofenamic acids, etc.).

All these products in spite of the undeniable progress that they have contributed to the field of treatment of the abovementioned disorders, have a major drawback which has prevented the use of these products with complete safety.

This drawback resides in the gastric aggressivity of these products, which makes it necessary to reduce notably the duration of the treatment or very often to interrupt it and moreover, to forbid its use in persons suffering from gastric and/or intestinal ulcers, even in the past and even if considered cured.

It is on the other hand frequent for the anthranilic or pyrazole derivatives to develop a hypersensitivity in the treated patient prohibiting all treatment.

OBJECTS AND SUMMARY OF THE INVENTION

Accordingly it is an object of the present invention to provide new non-steroidal anti-inflammatory medicaments which respond better to the requirements of pratice than previously known medicaments, notably by reason of their complete innocuousness and non-liability to cause any secondary reaction due to their good gastric tolerance, thus enabling treatment of long duration under conditions of complete safety.

According to the present invention there are provided novel medicaments with anti-inflammatory and analgesic action, characterized in that they correspond to the following general formula I:

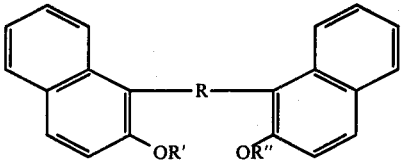

in which:
R represents an atom or sulfur or of oxygen or an $>SO$ or $>SO_2$ radical or even a

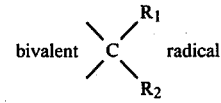

in which $R_1$ and $R_2$, which may be identical or different, represent a hydrogen atom or a hydroxyl, alkyl, aryl, arylalkyl, alkylaryl possibly halogenated radical or a heterocyclic radical, which radicals may be substituted or unsubstituted, whilst R' and R", which may be identical or different represent a hydrogen atom, a metal such as an alkali metal or alkaline-earth metal, or magnesium, or ammonium ion, or an alkyl radical, an aliphatic or aromatic acyl radical, or a heterocyclic radical, which radicals may be substituted or unsubstituted Certain of the compounds defined by the general formula I are known in themselves; this is the case notably for the compounds in which R represents the $>CH_2$ group (from formol) or $C_6H_5CH<$ (from benzaldehyde) for example.

Other compounds are novel and synthesized for the first time. This is the case notably for products in which R represents the residue of cuminaldehyde, vanilline, heliotropine, nicotinaldehyde, naphthaldehydes, p-tolualdehydes, fluorobenzaldehydes and trifluoromethylbenzaldehydes; these radicals can be substituted or unsubstituted.

Included among the compounds in accordance with the present invention are: di(2-hydroxy-1-naphthyl)sulphide; di(2-hydroxy-1-naphthyl)-methane; di(2-hydroxy-1-naphthyl)(3-fluoro-phenyl)-methane; di(2-hydroxy-1-naphthyl)(3-chloro-phenyl)-methane; di(2-hydroxy-1-naphthyl)(3-bromophenyl)-methane; di(2-hydroxy-1-naphthyl)(4-iodo-phenyl)-methane; di(2-hydroxy-1-naphthyl)(4-methyl-phenyl)-methane; di(2-hydroxy-1-naphthyl)(4-trifluoromethyl-phenyl)-methane; di(2-hydroxy-1-naphthyl)(3-methoxy-phenyl)-methane; di(2-hydroxy-1-naphthyl)(2-ethoxy-phenyl)-methane; di(2-hydroxy-1-naphthyl)(3-nitro-phenyl)-methane; di(2-hydroxy-1-naphthyl)(3-amino-phenyl)-methane; di(2-hydroxy-1-naphthyl)(3-acetamido-phenyl)-methane; di(2-hydroxy-1-naphthyl)(4-ethyl-phenyl)-methane; di(2-hydroxy-1-naphthyl)(4-isopropyl-phenyl)-methane; di(2-hydroxy-1-naphthyl)(3-4-dichloro-phenyl)-methane; di(2-hydroxy-1-naphthyl)(2-chloro-6-fluoro-phenyl)-methane; di(2-hydroxy-1-naphthyl)(4-chloro-3-nitro-phenyl)-methane; di(2-hydroxy-1-naphthyl)(2-4-dimethyl-phenyl)-methane; di(2-hydroxy-1-naphthyl)(2-3-dimethoxy-phenyl)-methane; di(2-hydroxy-1-naphthyl)(3-4-5-trimethoxy-phenyl)-methane; di(2-hydroxy-1-naphthyl)(3-hydroxy-phenyl)-methane; di(2-hydroxy-1-naphthyl)(4-hydroxy-3-methoxy-phenyl)-methane; di(2-hydroxy-1-naphthyl)(3-4-methylenedioxy-phenyl)- methane; di(2-hydroxy-1-naphthyl)(3-methyl-4-methoxy-phenyl)-methane; di(2-hydroxy-1-naphthyl)(2-3-dimethyl-4-methoxy-phenyl)-methane; di(2-hydroxy-1-naphthyl)(4-phenyl-phenyl)-methane; di(2-hydroxy-1-naphthyl)(2-naphthyl)-methane; di(2-hydroxy-1-naphthyl)(5-indanyl)-methane; di(2-hydroxy-1-naphthyl)(3-pyridyl)-methane; di(2-hydroxy-1-naphthyl)(2-quinoleyl)-methane.

Other compounds in accordance with the invention correspond to those in the last paragraph except that 2-hydroxy-1-naphthyl is replaced by 2-acetoxy-1-naphthyl.

Preferred compounds in accordance with the invention which have shown the best results in pharamocological tests include: di(2-hydroxy-1-naphthyl)(3-bromo-phenyl)-methane; di(2-hydroxy-1-naphthyl)(4-iodo-phenyl)-methane; di(2-acetoxy-1-naphthyl)(4-methyl-phenyl)-methane; di(2-acetoxy-1-naphthyl)-sulphide; di(2-acetoxy-1-naphthyl)-methane; di(2-hydroxy-1-naphthyl)(3-fluoro-phenyl)-methane; di(2-hydroxy-1-naphthyl)(3-4-dichloro-phenyl)-methane; di(2-hydroxy-1-naphthyl)(4-trifluoromethyl-phenyl)-methane.

According to another aspect of the present invention there are provided improvements in the process of preparing compounds of the general formula I, useful as medicaments.

The process of condensing β-naphthol with an aldehyde in an acetic medium has long been known (cf. Claisen, BERICHTE 19, 3316 (1886); Zenoni, GAZZETTA 23, (2), 218 (1896); Hewitt-Turner, BERICHTE 34, 202 (1901).

These authors react β-naphthol with the selected aldehyde, in an acetic medium in the presence of hydrochloric acid, crystallization taking place in acetic or alcoholic medium.

The preparation of the products of formula I according to the present invention, in following the protocols described by the various authors mentioned above, terminates inevitably in more or less considerable amounts of cyclization products (such as dibenzo [a,j] xanthenes), which are inactive. On the other hand, the bis-naphthols have the property of retaining polar solvents, such as acetic acid. Since medicaments are involved, the requirements of purity of the compounds are very much greater than in the case of the preparation of substances for non-therapeutic uses.

It is accordingly another object of the present invention to provide a process for the preparation of compounds corresponding to the general formula I above, by the action of β-naphthol on a suitable aldehyde, in acetic medium, in the presence of hydrochloric acid, said process being characterized in that it takes place at a temperature comprised between 5° and 10° C., in that the hydrochloric acid is added dropwise and in that the products obtained are purified by recrystallization from benzene or from a mixture of solvents containing benzene.

In a preferred embodiment of the process according to the present invention, precipitation is facilitated by the addition of sodium bicarbonate, in the case where the product obtained does not precipitate from the reaction solution.

In another advantageous embodiment of the process according to the present invention, a compound of the general formula I is converted into another compound of the same general formula, but having different substituents, by dissolution of the starting compound of formula I in a suitable solvent in the presence of an alkaline reducing reagent, endowed at the same time with solubilizing properties, such as hydrazine hydrate for example.

In another advantageous embodiment of the process according to the present invention, the derivatives in which R' and/or R" represent alkyl radicals, are obtained in the presence of small amounts of crystalline sodium acetate.

Besides the foregoing features, the present invention comprises still other features, which will emerge from the description which follows.

The present invention will be better understood with the aid of the ensuing description, in which examples of the operation of the process of preparation of the compounds of general formula I endowed with therapeutic properties, according to the present invention, will be found, as well as a report of the pharmacological experiments establishing the anti-inflammatory activity, the innocuousness and the good gastric tolerance of these novel medicaments.

It must be well understood, however, that these examples are given only by way of illustration of the invention and are not to be considered as in any way limiting.

DESCRIPTION OF THE PREFERRED EMBODIMENTS

Examples of Preparation

Example I: Preparation of 1-1' benzylidene-bis [2-naphthol]

$C_{27}H_{20}O_2$: MW = 376

14.4g (0.1 mole) of 2-naphthol are dissolved in 80 ml of acetic acid by slight warming. Solution being completed, it is cooled to a temperature around 5° C. and 5.3g (0.05 mol) of benzaldehyde is added. 8 ml of concentrated hydrochloric acid is added dropwise, whilst maintaining the temperature at about 5° C. When the addition is terminated, it is left to stand for 24 hours at 5° C. A white crystalline powder is deposited on the bottom of the container. It is sucked, washed with acetic acid so that the hydrochloric acid is quite removed, then it is recrystallized from benzene. 10.2 g of white crystalline powder melting at 216° C. (with decomposition), are obtained.

EXAMPLE II: Preparation of [3-pyridyl] bis (2-hydroxy-1-naphthyl)-methane $C_{26}H_{19}NO_2$: NW = 377

14.4 g (0.1 mole) of 2-naphthol are dissolved in 80 ml of acetic acid by warming slightly. It is left to cool to a temperature around 5° C. Then 5.35 g (0.05 mole) of nicotinaldehyde are added, then, whilst keeping the temperature at 5° C., 10 ml of concentrated HCl are added dropwise, with stirring. The solution is left for 8 days at the temperature of 5° C. At the end of this time, it is poured into 600 ml of water and little by little, 15 g of sodium bicarbonate is added whilst stirring to even out the effervescence. The white precipitate formed is sucked, then treated with boiling ethanol. It is left to cool and sucked.

After recrystallization, 6.7g of microcrystalline white powder melting at 245° C. with decomposition, is obtained.

EXAMPLE III: Preparation of 3-amino-benzylidene bis (2-naphthol)

$C_{27}H_{21}NO_2$: MW = 391

In a reflux flask, 4.2 g of 3-nitrobenzylidene bis (2-naphthol) is suspended in 100 ml of ethanol. 3 ml of hydrazine hydrate are added which has the effect of solubilizing the product. Then a spatula of Raney nickel is added. It is heated slightly whilst the hydrogen is released. After about ten minutes, the major portion of the nitro derivative is reduced and the slightly soluble amine starts to decompose on the walls. 30 ml of benzene are then added and it is brought to boiling. It is left under reflux for about half an hour. It is filtered hot to remove the nickel and the filtrate is concentrated to half its volume. It is allowed to cool; the precipitated crude amine is is recrystallized from an ethanolbenzene mixture.

The 3-amino-benzylidene bis (2-naphthol) obtained melts at 223° C.

EXAMPLE IV: Preparation of [2-naphthyl] bis (2-acetoxyl-1-naphthyl)-methane $C_{35}H_{26}O_4$: MW = 510

4.26 g (0.01 mole) of (2-naphthyl) bis (2-hydroxy-1-naphthyl) methane is dissolved in 20 ml of acetic anhydride at boiling point. To the solution some crystals of sodium acetate are added. It is heated under reflux for about 15 minutes. It is allowed to cool and transferred into 100 ml of ethanol. The precipitate is formed after some hours. It is sucked and recrystallized from an ethanol-benzene mixture.

3.9g (yield: 76%) of a white crystalline powder melting at 211° C. are obtained.

EXAMPLE V: Preparation of 2-hydroxy-2'methoxy-dinaphthyl (1)-methane $C_{22}H_{18}O_2$: MW = 314

15 g (0.05 mole) of 2-2' dihydroxy dinaphthyl (1)-methane are dissolved in a boiling solution of 4 g of soda in pellets in 100 ml of water. It is allowed to cool and the monosodium salt crystallizes. The precipitate is sucked and resuspended in 100 ml of water to which 4 ml of methyl sulfate are added. It is heated moderately for about 15 minutes. At the end of this time, the reaction mass is sucked, ground in a mortar, treated with a hot solution of 4 g of NaOH in 100 ml of water and finally washed vigorously with water, sucked, dried and recrystallized.

A crystalline white powder melting at 148° C. is obtained.

The research carried out by the inventor has established that the compounds which correspond to the general formula I, both those which were known and those newly synthesized by the inventor, possess remarkable anti-inflammatory properties, whilst having a very substantially lower gastric agressivity than that of all the previously known medicaments for these therapeutic purposes.

These remarkable therapeutic properties of the novel medicaments according to the invention, have been established in the course of pharmacological experiments of which an account will be given below, with reference by way of example, purely to illustrate the invention and without being of any limiting nature, to some of the compounds according to the invention.

Report of pharmacological experiments carried out to establish the therapeutic properties of the compounds of the general formula I A. Toxicological study Acute Toxicity — Oral Route measured in male mice, of the NMRI Han.EOPS Swiss breed weighing 20–22 grams.

Administration by gastric intubation, at the dose of 0.5 ml per 20 grams of body weight, of aqueous suspensions of the various derivatives in the presence of gum arabic.

Examination of the animals: 8 days.

TABLE I

| PHENOL DERIVATIVES | | | |
|---|---|---|---|
| PRODUCT | MTD mg/kg | LD$_{50}$ mg/kg | mLD mg/kg |
| 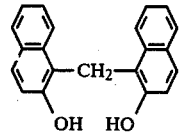 | 2000 | 5600 | 11000 |
| 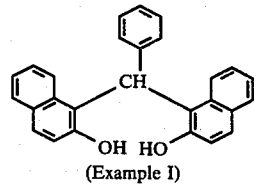 (Example I) | ≧2500 | >2500 | >2500 |
| 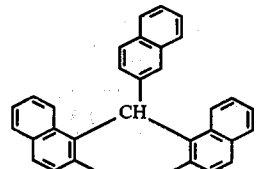 | ≧2500 | >2500 | >2500 |
| 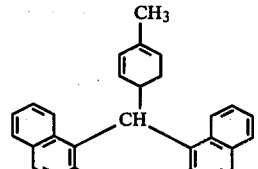 | ≧2500 | >2500 | >2500 |

| BIS CORRESPONDING ACETYLATED DERIVATIVES | | | |
|---|---|---|---|
| PRODUCT | MTD mg/kg | LD$_{50}$ mg/kg | mLD mg/kg |
| 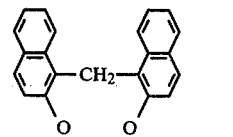 | ≧2500 | >2500 | >2500 |
| 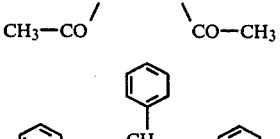 | ≧3000 | >3000 | >3000 |

TABLE I-continued

[Structure: bis(2-naphthyl) diacetate with 2-naphthyl CH bridge] (Example IV) — ≧2500   >2500   >2500

[Structure: bis(2-naphthyl) diacetate with p-tolyl CH bridge] — ≧2500   >2500   >2500

MTD = Maximum Tolerated Dose (LD$_o$)
mLD = minimum Dose which is always lethal (LD$_{100}$)

It is recalled that the MTD, the mLD and the LD$_{50}$ of the known compounds are as follows:

| | | |
|---|---|---|
| Flufenamic acid : | MTD | 250 mg/kg |
| | LD$_{50}$ | 1000 mg/kg |
| | mLD | 1500 mg/kg |
| Oxyphenbutazone : | MTD | 250 mg/kg |
| | LD$_{50}$ | 1000 mg/kg |
| | mLD | 1500 mg/kg |
| Aspirin micrograins : | MTD | 1500 mg/kg |
| | LD$_{50}$ | 2150 mg/kg |
| | mLD | 3000 mg/kg |

Acute Toxicity — Intraperitoneal Route measured in male mice of the NMRI Hans EOPS breed weighing 20–22 grams.

0.5 ml per 20 grams of body weight of suspensions in the presence of gum arabic, of the various derivatives in isotonic NaCl solution.

Examination of the animals: 8 days.

TABLE II

PHENOL DERIVATIVES

| PRODUCT | MTD mg/kg | LD$_{50}$ mg/kg | mLD mg/kg |
|---|---|---|---|
| [bis-2-naphthol CH$_2$ bridge] | 1000 | 1950 | 3000 |
| [bis-2-naphthol CH-phenyl bridge] (Example I) | ≧2500 | >2500 | >2500 |

TABLE II-continued

PHENOL DERIVATIVES

| PRODUCT | MTD mg/kg | LD$_{50}$ mg/kg | mLD mg/kg |
|---|---|---|---|
| [bis-2-naphthol CH-(2-naphthyl) bridge] | ≧1000 | >1000 | >1000 |
| [bis-2-naphthol S bridge] | | 500 | 1000 to 1500 |
| [bis-2-naphthol CH-(p-tolyl) bridge] | ≧1000 | >1000 | >1000 |

TABLE II BIS

CORRESPONDING ACETYLATED DERIVATIVES

| PRODUCT | MTD mg/kg | LD$_{50}$ mg/kg | mLD mg/kg |
|---|---|---|---|
| [bis-2-acetoxynaphthyl CH$_2$ bridge] | ≧1000 | >1000 | >1000 |
| [bis-2-acetoxynaphthyl CH-phenyl bridge] | ≧1500 | >1500 | >1500 |
| [bis-2-acetoxynaphthyl CH-(2-naphthyl) bridge] | ≧1000 | >1000 | >1000 |
| [bis-2-acetoxynaphthyl S bridge] | | 500 | 1000 to 1500 |

TABLE II-continued
PHENOL DERIVATIVES

| | | | |
|---|---|---|---|
| (structure: CH₃-C₆H₄-CH linking two naphthyl groups with O-CO-CH₃ substituents) | ≧1000 | >1000 | >1000 |

MTD = Maximum Tolerated Dose (LD$_o$)
mLD = minimum dose which is always lethal (LD$_{100}$)

The MTD, the mLD and the LD$_{50}$ of the following known compounds, are indicated below:

| | | |
|---|---|---|
| Flufenamic acid : | MTD | 100 mg/kg |
| | LD$_{50}$ | 320 mg/kg |
| | mLD | 500 mg/kg |
| Oxyphenbutazone : | MTD | 100 mg/kg |
| | LD$_{50}$ | 147.5 mg/kg |
| | mLD | 200 mg/kg |

B. Study of gastric aggressivity in the Rat

The confirmation, in the animal, of the gastro-duodenal aggressivity of anti-inflammatory substances requires the generation of experimental conditions which are much more severe than the clinical conditions: doses, gastric vacuity, placing under semi-compulsion, are so many factors which the experimenter can modify to sensitize the animals to the aggressive effects of the derivatives under test.

Principle

The administration of high doses of anti-inflammatory derivatives to fasting animals under experimental conditions conducive to the development of experimental ulcers, is followed by the appearance of signs of gastric aggressivity which involve comparative evaluation.

Animal Stock

WISTAR AF.Han.EOPS rats of the male sex weighing 120-140 g.

Technique

After rigorous fasting for 26 hours the animals in batches of 10, receive by the digestive route, by gastric intubation, in a uniform volume of 1 ml/100 g of body weight, a medicinal suspension in a pseudo-solution of 10% gum arabic the doses administered being 100, 250 or 500 mg/kg as the case may be.

The animals are then placed in semi-constraint in small cages for 22 hours.

After 48 hours of fasting namely, 22 hours after the medicinal administration, the animals are sacrificed by venesection. The stomachs are removed, slit longitudinally along the greater curvature, carefully rinsed under a stream of isotonic sodium chloride solution then spread out on cork.

The gastric damage is estimated according to a personal quotation taking into account the existence and the seriousness of the irritated and ulcerated areas.

TABLE III
Gastric Aggressivity In The Rat

| Evaluation Of The Ulcers | Evaluation Of Hyperhemia |
|---|---|
| 0 = ulcer absent | 0 = absence of hyperhemia |
| 0.5 = one or two points of ulceration present | 0.5 = slight diffused irritation |
| 1 = distinct ulceration at two to three points | 1 = one distinctly red area |
| 2 = two ulcerations at 4 points | 2 = several congested areas |
| 3 = distinct and numerous ulcerations | 3 = entirely inflamed |

It is possible to calculate indices of ulceration and of irritation or hyperhemia (I), taking into account the number of animals having changes in their gastric wall and the size of the lesions.

$$I = \frac{\text{Sum of evaluations} \times \text{percentage affected}}{\text{number of animals}}$$

Taking into account the greater importance which should be given to ulcerations than to signs, moreover easily reversible, of hyperhemia, an overall index of gastric aggressivity is then calculated by adding to the index of hyperhemia (IH) treble the index of ulceration (IU):

Overall index of gastric aggressivity = IH + 3 IU

Parallel with the study of the anti-inflammatory activity with respect to carrageenin oedema, it was possible to apply a less severe test for estimating the gastric aggressivity:

The rats were sacrificed after only 24 hours of fasting and only 5 hours after the administration of the anti-inflammatory substance.

TABLE IV
GASTRIC AGGRESSIVITY IN THE RAT

Protocol : 0h fasting commenced
26h oral treatment
48h sacrifice

| Compound of formula I | Dose mg/kg | Ulcer Index | Hyperhemia Index | Overall Index |
|---|---|---|---|---|
| (dinaphthyl-CH₂ with OH HO) | 250 | 4.5 | 2 | 15.5 |
| (dinaphthyl-CH₂ with OH HO) | 500 | 6 | 10 | 28 |
| (dinaphthyl-CH with phenyl, OH HO) (Example I) | 250 | 7.5 | 0.5 | 23 |
| (dinaphthyl-CH₂ with O-CO-CH₃, CH₃-CO-O) | 250 | 20 | 22.5 | 82.5 |

TABLE IV-continued

GASTRIC AGGRESSIVITY IN THE RAT

Protocol: 0h fasting commenced
26h oral treatment
48h sacrifice

| Compound of formula I | Dose mg/kg | Ulcer Index | Hyperhemia Index | Overall Index |
|---|---|---|---|---|
| (CH with phenyl, two naphthyl-O-CO-CH3) | 250 | 20 | 12 | 72 |
| (CH with 2-naphthyl, two naphthyl-OH) | 250 | 18 | 16 | 70 |
| (CH with p-tolyl-CH3, two naphthyl-OH) | 250 | 12 | 8 | 44 |
| Known compounds | | | | |
| Aspirin | 250 | 104 | 18 | 330 |
| Oxyphenbutazone | 250 | 200 | 2 | 602 |
| Oxyphenbutazone | 100 | 188 | 12 | 576 |
| Flufenamic acid | 250 | 240 | 22 | 742 |
| Flufenamic acid | 100 | 216 | 14 | 662 |

TABLE V

GASTRIC aggressivity in the rat

Protocol: 0 h commencement of fasting
19 h oral treatment
24 h sacrifice

| Compound of Formula I | Dose mg/kg | Ulcer Index | Hyperhemia Index | Overall Index |
|---|---|---|---|---|
| (CH2 bridge, two naphthyl-OH) | 250 | 9 | 1 | 28 |
| (Example I) (CH with cyclohexadienyl, two naphthyl-OH) | 250 | 9 | 15 | 42 |
| (CH2 bridge, two naphthyl-O-CO-CH3) | 250 | 6 | 21 | 39 |
| (CH with phenyl, two naphthyl-O-CO-CH3) | 250 | 15 | 9 | 54 |
| (CH with 2-naphthyl, two naphthyl-OH) | 250 | 25 | 8 | 83 |
| Known compounds | | | | |
| Oxyphenbutazone | 100 | 112 | 50 | 386 |
| Flufenamic acid | 50 | 91 | 15 | 288 |

C. Study of anti-inflammatory activity

CARRAGEENIN OEDEMA IN THE MOUSE OR THE RAT

Principle

The injection of carrageenin under plantar aponeurosis of a rear paw in the Rat or in the Mouse causes an inflammatory reaction which can be reduced by anti-inflammatory substances.

Animal Stock

Male or female rats of the AF. Han. EOPS WISTAR race weighing 100–120 g body weight.

Male mice of the SWISS NMRI Han. EOPS breed

Method

The rats (10 per substance) are subjected to fasting conditions since the eve of the test, namely 18 hours before the start of the latter.

The mice are not subjected to fasting.

At zero time, the carrageenin is injected into the plantar pad of a rear paw, at the dose of 0.05 ml of a 1% suspension in sterile bidistilled water. One hour later the animals are treated with the anti-inflammatory substances. The animals were sacrificed at the sixth hour. The amputation of the two rear paws was carried out, and they were weighed. The average inflammation was then determined per hundred (by the difference in weight between the inflamed paw and the uninflamed paw).

The anti-inflammatory activity is calculated as a percentage reduction of the inflammatory oedema in the treated animals with respect to the control animals which had only received the carrageenin without any treatment.

In the case of the rats there was also an examination of the stomachs.

INFLUENCE ON KAOLIN OEDEMA IN THE MOUSE OR THE RAT

Principle and Animal Stock

Identical with those described for the carrageenin oedema; 0.05 ml of a 10% suspension of kaolin in sterile bidistilled water.

| | Method | |
|---|---|---|
| Mice : | zero time | kaolin |
| | 2 hours | treatment |
| | 18 hours | sacrifice - amputations - weighings |
| Rats : | zero time | fasting commenced |
| | 24 hours | kaolin |
| | 26 hours | treatment |
| | 48 hours | sacrifice - amputations - weighings |
| | | Examination of the stomachs after 48 h fasting |

1. INFLUENCE EXERTED ON CARRAGEENIN OEDEMA IN THE MOUSE

TABLE VI

Protocol : 0-1-6 hours
Derivatives according to the invention, administered at the dosage of 250 mg/kg per os
10 animals per test
The anti-inflammatory activity (AIA) is expressed as a percentage reduction of oedema in the treated animals with respect to the controls.

| Compound of Formula I | Test No 1 AIA % | Test No 2 AIA % | Test No 3 AIA % | Test No 4 AIA % | Average Results AIA % |
|---|---|---|---|---|---|
| 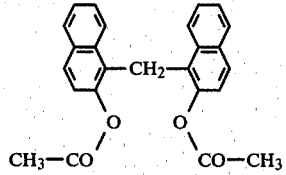 | 18.23 | | | | 18.23 |
| 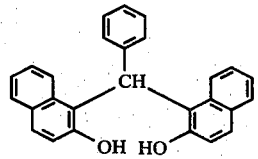 (Example I) | 18.32 | 20.83 | 19.62 | | 19.59 |
| 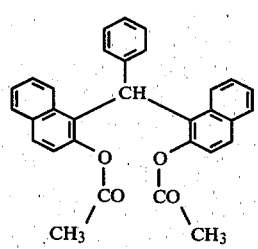 | 27.89 | 25.63 | 25.92 | | 26.48 |
| 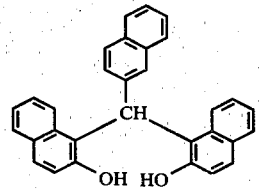 | 27.33 | 37.96 | 19.66 | | 28.31 |
| 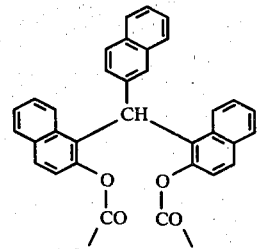 (Example IV) | | | | | 25.50 | 25.50 |

TABLE VI-continued

Protocol: 0-1-6 hours
Derivatives according to the invention, administered at the dosage of 250 mg/kg per os
10 animals per test
The anti-inflammatory activity (AIA) is expressed as a percentage reduction of oedema in the treated animals with respect to the controls.

| Compound of Formula I | Test No 1 AIA % | Test No 2 AIA % | Test No 3 AIA % | Test No 4 AIA % | Average Results AIA % |
|---|---|---|---|---|---|
| [naphthyl-S-naphthyl with OH, HO] | | | 22.82 | | 22.82 |
| [naphthyl-S-naphthyl with O-CO-CH3 groups] | | | 28.22 | | 28.22 |
| [bis-naphthyl-CH with p-tolyl, OH HO] | | | 25.53 | 21.15 | 23.34 |
| [bis-naphthyl-CH with p-tolyl, O-CO-CH3 groups] | | | | 27.97 | 27.97 |
| "Rhodine" (Aspirin in micrograins) 250 mg/kg | | | 29.10 | | |

2. INFLUENCE ON KAOLIN OEDEMA IN THE MOUSE

TABLE VII

Protocol: 0-2-18 hours
Derivatives according to the invention, administered at the dose of 250 mg/kg orally
10 animals per test
Anti-inflammatory activity (AIA) expressed as percentage reduction of oedema of the treated animals with respect to the controls.

| Compound of Formula I | Test No 1 AIA % | Test No 2 AIA % | Test No 3 AIA % | Test No 4 AIA % | Test No 5 AIA % | Average Results AIA % |
|---|---|---|---|---|---|---|
| [naphthyl-CH2-naphthyl with OH, HO] | 23.03 | 25.64 | | | | 24.33 |

TABLE VII-continued

Protocol: 0-2-18 hours
Derivatives according to the invention, administered
at the dose of 250 mg/kg orally
10 animals per test
   Anti-inflammatory activity (AIA) expressed as
percentage reduction of oedema of the treated animals with
respect to the controls.

| Compound of Formula I | Test No 1 AIA % | Test No 2 AIA % | Test No 3 AIA % | Test No 4 AIA % | Test No 5 AIA % | Average Results AIA % |
|---|---|---|---|---|---|---|
| [structure: bis-naphthyl CH₂ with OCOCH₃ groups] | | | 22.73 | 22.61 | | 22.67 |
| [structure: bis-naphthol with CH-phenyl] (Example I) | | | 27.72 | 27.72 | | 27.72 |
| [structure: bis-naphthyl acetate with CH-phenyl] | | | 28.40 | 30.12 | 18.58 | 25.70 |
| [structure: bis-naphthol with CH-naphthyl] | | | | | 18.76 | 18.76 |
| [structure: bis-naphthyl acetate with CH-naphthyl] (Example IV) | | | | 23.72 | | 23.72 |
| [structure: bis-naphthol with S bridge] | | | | | 25.15 | 25.15 |
| [structure: bis-naphthyl acetate with S bridge] | | | | | | |

TABLE VII-continued

Protocol: 0-2-18 hours
Derivatives according to the invention, administered
at the dose of 250 mg/kg orally
10 animals per test
Anti-inflammatory activity (AIA) expressed as
percentage reduction of oedema of the treated animals with
respect to the controls.

| Compound of Formula I | Test No 1 AIA % | Test No 2 AIA % | Test No 3 AIA % | Test No 4 AIA % | Test No 5 AIA % | Average Results AIA % |
|---|---|---|---|---|---|---|
| 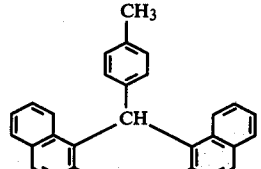 | | | | 25.79 | 24.09 | 24.94 |
| 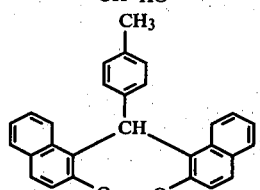 | | | | | 25.27 | 25.27 |
| Known compounds "Rhodine" 250 mg/kg | | | | 14.40 | | |
| Oxyphenbutazone 250 mg/kg | 17.92 | | | | | |

3. INFLUENCE ON CARRAGEENIN OEDEMA IN THE WISTAR RAT

TABLE VIII

Protocol: 0-1-6 hours fasting for 18 hours
treatment 250 mg/kg orally
10 animals per test
Anti-inflammatory activity (AIA) expressed as
the percentage reduction in oedema in the treated
animals with respect to the control animals.

| Compound of Formula I | Test No 1 AIA % | Test No 2 AIA % |
|---|---|---|
| 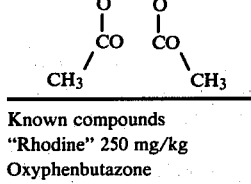 | 21.17 | |
| | 16.29 | |
| 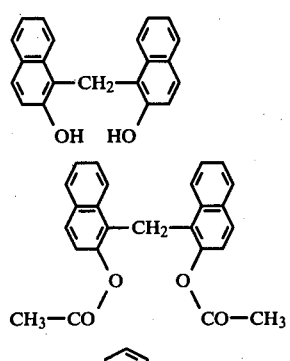 (Example I) | 30.30 | |

TABLE VIII-continued

Protocol: 0-1-6 hours fasting for 18 hours
treatment 250 mg/kg orally
10 animals per test
Anti-inflammatory activity (AIA) expressed as
the percentage reduction in oedema in the treated
animals with respect to the control animals.

| Compound of Formula I | Test No 1 AIA % | Test No 2 AIA % |
|---|---|---|
| 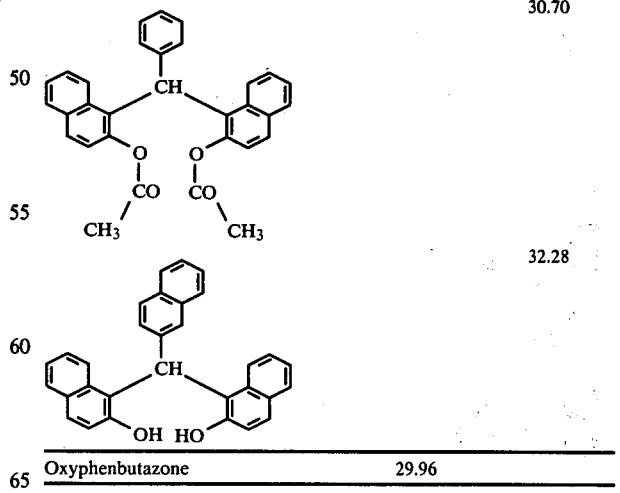 | 30.70 | |
| | 32.28 | |
| Oxyphenbutazone | 29.96 | |

4. INFLUENCE ON CARRAGEENIN OEDEMA IN THE WISTAR RAT

TABLE IX

Protocol: 0-1-6 hours after fasting for 18 hours treatment 100 mg/kg by the intraperitoneal route

ANTI-INFLAMMATORY ACTIVITY

| Compound of the Formula I | MALE RATS AIA % | FEMALE RATS AIA % | MEAN MALE FEMALE AIA % |
|---|---|---|---|
| (naphthyl-CH₂-naphthyl with OH, HO) | 18.44 | 22.37 | 20.40 |
| (Example I) | 23.97 | 24.75 | 24.36 |
| (naphthyl-CH₂-naphthyl with O-CO-CH₃, CH₃-CO-O) | 22.86 | 24.44 | 23.65 |

5. INFLUENCE ON KAOLIN OEDEMA IN THE WISTAR RAT

TABLE X

Protocol: 0-2-24 hours after fasting for 24 hours treatments 250 mg/kg by the oral route

| Compound of Formula I | Test No 1 AIA % | Test No 2 AIA % |
|---|---|---|
| (naphthyl-CH₂-naphthyl with OH, HO) | 28.74 | 11.99 |
| (Example I) | | 17.26 |
| (naphthyl-CH-naphthyl with O-CO-CH₃, CH₃-CO-O) | | 22.83 |
| Oxyphenbutazone (known compound) | 36.83 | 29.84 |

It is shown by the pharmacological properties which have just been described, that the new medicaments according to the invention must be considered as preferred anti-inflammatory agents, as much for their anti-inflammatory and analgesic action as for their very low toxicity and especially for their remarkable tolerance resulting from their low gastric aggressivity in comparison with previously known medicaments.

The novel medicaments according to the invention may be administered alone or in association with other medicaments and in various suitable dosage forms, especially orally, parenterally and rectally, etc.

These compounds of the present invention may be associated with suitable pharmaceutical vehicles e.g. as suspensions in water, in capsules, in tablets, in injectable solution, in suppositories, etc. by methods known per se.

The normal dosage range is from about 100 mg. to about 250 mg. of the active principle per unit dose. The normal posology is administration to the patient at the rate of 3 to 6 times per day.

I claim:

1. Method of treating patient suffering from painful and inflammatory conditions comprising administering to the patient, in an analgesic and anti-inflammatory effective amount, a composition comprising a pharmaceutical carrier and, as active principle, at least one compound of the formula:

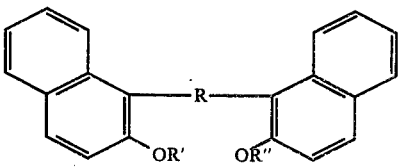

wherein:

R is a

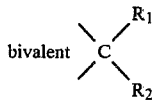

radical in which $R_1$ and $R_2$, which can be the same or different, represent hydrogen, hydroxyl, phenyl, naphthyl, alkyl, or phenyl substituted by $C_{1-3}$ alkyl, $C_{1-2}$ alkoxy, halogen, hydroxy, $NH_2$, $CF_3$, $NHOCOCH_3$, or phenyl; and wherein R' and R", which can be the same or different, represent a hydrogen atom, a halogen atom, a metal selected from the group consisting of alkali metals, alkaline earth metals and magnesium, or the ammonium ion.

2. A method in accordance with claim 1, wherein said method comprises administering said composition at a dosage corresponding to between 300 mg and 1500 mg of the active principle per day.

3. The method of claim 1, wherein R represents an unsubstituted benzaldehyde residue and R' and R" are different.

4. The method in accordance with claim 1 wherein the active principle is di(2-hydroxy-1-naphthyl)(3-bromo-phenyl)-methane.

5. The method in accordance with claim 1 wherein the active principle is di(2-hydroxy-1-naphthyl)(4-iodo-phenyl)-methane.

6. The method in accordance with claim 1 wherein the active principle is di(2-hydroxy-1-naphthyl)(3-fluoro-phenyl)-methane.

7. The method in accordance with claim 1 wherein the active principle is di(2-hydroxy-1-naphthyl)(3-4-dichloro-phenyl)-methane.

8. The method in accordance with claim 1 wherein the active principle is di(2-hydroxy-1-naphthyl)(4-trifluoromethyl-phenyl)-methane.

9. The method according to claim 1, wherein R' and R" comprise an alkali or alkaline-earth metal.

10. The method according to claim 1 wherein the active principle is 1,1' benzylidene-bis.

11. A method in accordance with claim 1 wherein, in said composition, R represents

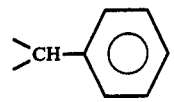

in which the phenyl radical is unsubstituted or substituted by $C_{1-3}$ alkyl, $C_{1-2}$ alkoxy, halogen, hydroxy, $NH_2$, $CF_3$, $NHOCOCH_3$, or phenyl.

12. The method of claim 11 wherein R' and R" are both hydrogen atoms.

13. A method in accordance with claim 1, wherein $R_2$ is H.

* * * * *